(12) United States Patent
Hemphill et al.

(10) Patent No.: US 9,011,786 B2
(45) Date of Patent: Apr. 21, 2015

(54) DRY HEAT STERILIZING SYSTEMS USING INDUCTIVE HEATING

(75) Inventors: William K. Hemphill, Johnson City, TN (US); Martin P. Eason, Johnson City, TN (US); Martin E. Olson, Johnson City, TN (US); J. Paul Sims, Greeneville, TN (US)

(73) Assignee: State of Franklin Innovations, LLC, Johnson City, TN (US)

( * ) Notice: Subject to any disclaimer, the term of this patent is extended or adjusted under 35 U.S.C. 154(b) by 899 days.

(21) Appl. No.: 13/036,556

(22) Filed: Feb. 28, 2011

(65) Prior Publication Data

US 2011/0211989 A1 Sep. 1, 2011

Related U.S. Application Data

(60) Provisional application No. 61/308,511, filed on Feb. 26, 2010.

(51) Int. Cl.
*B01J 19/12* (2006.01)
*A61L 2/00* (2006.01)
*A61L 2/06* (2006.01)

(52) U.S. Cl.
CPC .............. *A61L 2/06* (2013.01); *A61L 2202/122* (2013.01); *A61L 2202/24* (2013.01)

(58) Field of Classification Search
CPC .............................. A61L 2/06; A61L 2202/24
USPC ................................................ 422/186.06, 22
See application file for complete search history.

(56) References Cited

U.S. PATENT DOCUMENTS

| | | | | |
|---|---|---|---|---|
| 5,575,082 A * | 11/1996 | Kishi | ............................... | 34/247 |
| 5,607,612 A * | 3/1997 | Held et al. | ..................... | 219/759 |
| 5,645,748 A * | 7/1997 | Schiffmann et al. | .......... | 219/710 |
| 6,008,482 A * | 12/1999 | Takahashi et al. | ............. | 219/687 |
| 2003/0132279 A1* | 7/2003 | Stemmle | ......................... | 232/31 |

* cited by examiner

*Primary Examiner* — Kevin Joyner
(74) *Attorney, Agent, or Firm* — Dinsmore & Shohl LLP (57) ABSTRACT

A dry heat sterilizing system for use in sterilizing non-ferromagnetic and/or ferromagnetic parts includes a sterilization chamber and at least one ferromagnetic structure within the sterilization chamber. At least one inductive EMF energy field generator inductively heats the at least one ferromagnetic structure during a sterilization operation. The at least one ferromagnetic structure is in thermal communication with the non-ferromagnetic and/or ferromagnetic part during a sterilization operation to transfer heat from the ferromagnetic structure to the non-ferromagnetic and/or ferromagnetic part.

17 Claims, 4 Drawing Sheets

DRY HEAT STERILIZING SYSTEMS USING INDUCTIVE HEATING

CROSS-REFERENCE TO RELATED APPLICATIONS

This application claims priority to U.S. Provisional Application No. 61/308,511, filed Feb. 26, 2010, the details of which are incorporated by reference in their entirety.

TECHNICAL FIELD

The present specification generally relates to the field of transferring dry heat to one or more tools, such as medical instrumentation, for the purpose of sterilization. With this design, there is decreased energy consumption; thus it is also directed at the fields of devices to increase the efficiency of commercial appliances. With this design, there is no use of closed pressure vessels or hazardous chemicals; thus it is additionally directed at the fields of devices to increase the safety of commercial appliances.

BACKGROUND

Various methods of sterilization in medical and laboratory environments include autoclave technology (a wet heat transfer process involving the use of superheated steam in a sealed pressure vessel), Gamma ray technology (a sterilization technique bombarding the target with high energy radiation), and high temperature oven technology (a dry heat transfer process involving the use of gas or electrical resistance heating elements). However, the devices associated with these technologies are often relatively large and non-portable and include numerous sterilization steps.

SUMMARY

In one embodiment, a dry heat sterilizing system for use in sterilizing non-ferromagnetic and/or ferromagnetic parts includes a sterilization chamber and at least one ferromagnetic structure within the sterilization chamber. At least one inductive EMF energy field generator inductively heats the at least one ferromagnetic structure during a sterilization operation. The at least one ferromagnetic structure is in thermal communication with the non-ferromagnetic and/or ferromagnetic part during a sterilization operation to transfer heat from the ferromagnetic structure to the non-ferromagnetic and/or ferromagnetic part.

In another embodiment, a method of sterilizing a non-ferromagnetic medical instrument using a dry heat sterilizing system is provided. The method includes placing the medical instrument in a sterilization chamber of the sterilizing system such that the medical instrument is in thermal communication with at least one ferromagnetic structure within the sterilization chamber during a sterilization operation. The at least one ferromagnetic structure is inductively heated during the sterilization operation using an inductive EMF energy field generator whereby the medical instrument is heated due to the thermal communication with the ferromagnetic structure.

In another embodiment, a dry heat sterilizing system for use in sterilizing non-ferromagnetic medical instruments includes a sterilization chamber and a field of loose ferromagnetic beads located within the sterilization chamber. At least one inductive EMF energy field generator inductively heats the loose ferromagnetic beads during a sterilization operation. A superheating system has an inlet for receiving heated gas from the sterilization chamber and an outlet for re-introducing heated gas to the sterilization chamber. The superheating system includes a superheating structure comprising a ferromagnetic material such that, once inductively heated, the superheating structure transfers heat to the heated gas prior to re-introduction to the sterilization chamber.

In another embodiment, a device for sterilizing ferromagnetic or non-ferromagnetic part(s) or assembly(ies) (e.g., instrument, vessel, apparatus, &/or device) comprising at least one inductive EMF energy field generator, at least one inductively-heated ferromagnetic surface or at least one inductively-heated bed/matrix of ferromagnetic media (or non-ferromagnetic heat transfer media) in thermal communication with the part or assembly to be sterilized; and at least one control logic system with associated sensors and actuators. More specific embodiments include: devices where in the at least one inductive EMF energy field generator further comprises an apparatus capable of generating at least one controlled, oscillating electromagnetic field; devices wherein the at least one inductively-heated ferromagnetic surface further comprises the at least one inductive EMF energy field generator, wherein the inductively-heated ferromagnetic surface is comprised of at least one ferromagnetic material wherein the at least one ferromagnetic material
  a. is in the region of influence of the oscillating electromagnetic field generated by the inductive EMF energy field generator and
  b. is in thermal communication with
     i. the part or assembly to be sterilized
     ii. a bagging material that encloses the part or assembly to be sterilized and/or
     iii. the bed/matrix of non-ferromagnetic heat transfer media.

In particular embodiments the at least one inductively-heated bed/matrix of ferromagnetic media further comprises the at least one inductive EMF energy field generator wherein the inductively-heated bed/matrix of ferromagnetic media is
  c. in the region of influence of the oscillating electromagnetic field generated by the inductive EMF energy field generator and
  d. is in thermal communication with
     i. the part or assembly to be sterilized or
     ii. a bagging material that encloses the part or assembly to be sterilized.

In other specific embodiments the at least one control logic system with associated sensors and actuators further comprises
  e. at least one logic unit for controlling the at least one oscillating electromagnetic field generated by the at least one inductive EMF energy field generator, and
  f. a plurality of sensors to measure the temperature of the inductively heated surface, control set points, and user inputs, and
  g. at least one actuator for locking the access door, and/or positioning a sealing mechanism.

According to further specific embodiments, the at least one actuator for positioning a sealing mechanism further comprises a sealing method/mechanism involving the at least one control logic system and
  h. electrical resistance, thermal, or ultrasonic welding;
  i. thermal or pressure-activated bonding; &/or
  j. mechanical seaming and sealing The invention also provides methods of sterilizing at least one part or assembly comprising application of the devices in accordance with the invention.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

The embodiments shown in the figures are representative in nature and do not show the true spatial relationships among the various components (i.e., the distance between the inductive EMF force field generator and the ferromagnetic materials). It should also be noted that the figures showing these various and several embodiments illustrate neither device enclosure configurations nor the placement of necessary thermal and electrical insulating materials and/or sealing/seaming mechanisms.

DETAILED DESCRIPTION

Apparatus and methods described herein generally relate to the use magnetic induction to provide the dry heat necessary to elevate quickly instruments, tools, and assorted appliances used in medical, dental, veterinary, laboratory, commercial, and industrial applications to a temperature sufficient for sterilization. Embodiments may be suitable for use as a Class II, dry-heat sterilizer intended for use by a health care provider to sterilize medical products by means of dry heat (IAW 21CFR880.6870); an office, laboratory, or personal sterilizer; a rapid sterilizer for single or dropped tools; and a sterilizer for use in developing countries and military/humanitarian deployment theatres where traditional wet or chemical sterilization technologies and methods are generally unavailable, non-maintainable, or contraindicated and where traditional dry heat technologies and methods are considered too slow or inefficient.

Embodiments may be suitable for use as a "desktop" or standalone devices for sterilizing and bagging implements for subsequent use in a medical office, operating theatre, laboratory, ambulance, kit, or a home and as a non-bagging, quick-turnaround device for sterilizing dropped instruments and/or biologically contaminated implements in a hospital, operating room, portable surgical theatre, or anywhere where electrical power can be used or generated.

Magnetic induction is a method to heat ferromagnetic materials placed within close proximity to a generated magnetic field. Magnetic induction may be used to heat ferromagnetic materials in industrial uses by exposing the material to be heated within the magnetic field. Embodiments described herein incorporate inductive heating as a sterilizing method. Where non-ferromagnetic materials are used in the manufacture of an implement to be sterilized, the implement can be placed in immediate contact with one or more inductively heated, ferromagnetic surfaces and use the principle of conductive heat transfer to bring the implement to a temperature sufficient to ensure sterility. These inductively heated, ferromagnetic surfaces include but are not limited to a flat surface; one or two-sided flexible foil bags or tubes; and/or a matrix of small "bead-like" media that can be mechanically or pneumatically agitated to ensure sufficient contact and thermal heat transfer.

Figure 1:
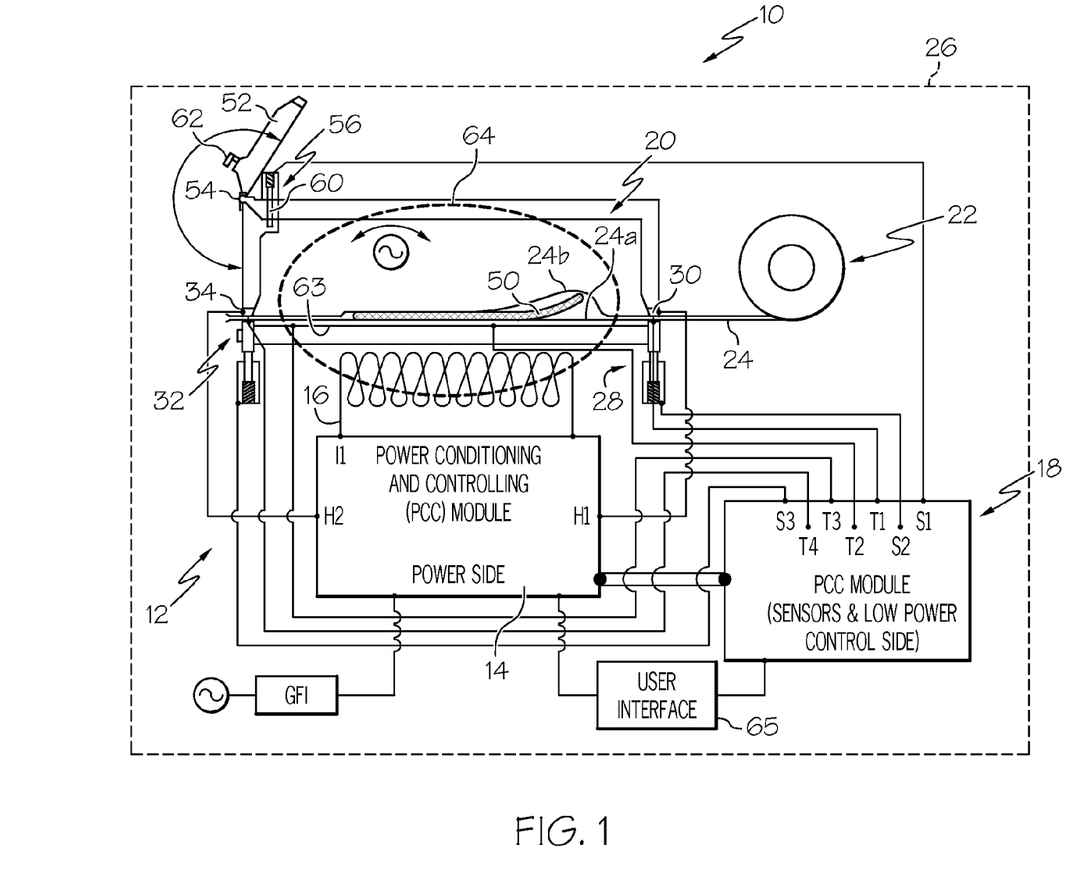
FIG. 1 illustrates a system schematic of a bagging-type sterilizer embodiment using a roll of sleeving material or flattened tube for bagging in conjunction with a single inductively heated surface.

Referring to FIG. 1, an exemplary sterilizing system 10 includes an inductive EMF energy field generator 12 including a power conditioning and control module 14 and an induction coil 16, a controller module 18 that receives inputs from one or more sensors and/or control devices, a sterilization chamber 20 in proximity to the induction coil 16 and a roll 22 of continuous sleeving material 24. In some embodiments, the field generator 12, controller module 18, sterilization chamber 20 and roll 22 of continuous sleeving material 24 may all be housed within the same housing structure 26. In other embodiments, one or more of the various components (e.g., the roll 22 of sleeving material 24) may be located outside the housing structure 26. Further, the housing structure 26 may be formed of a non-ferromagnetic material and may provide magnetic shielding to prevent or reduce passage of magnetic fields through the housing structure 26.

The EMF energy field generator 12 includes the power conditioning and control module 14 and the induction coil 16. AC power may be supplied to the induction coil 16 from the power conditioning and control module 14. In some embodiments, an inverter may be used to convert a DC input to the AC power. The induction coil 16 may comprise any suitable inductor and may be a single or multiple turn inductor coil, or an assembly of individual inductor coils. The inductor coil 22 can operate at any frequency and power that is required for a particular application. For example, in certain embodiments, the inductor operates at a power between 1000 W-3000 W and at a frequency of 1 kHz-400 kHz.

The sterilizing system 10 may further include various sleeve material handling features. For example, a first cutting and sealing device 28 may be located at a sleeve entrance location 30 at the sterilization chamber 20 and a second cutting and sealing device 32 may be located at an access opening 34 to the sterilization chamber 20. Any suitable cutting and sealing devices 28 and 32 may be used suitable for severing the sleeving material 24 and forming a hermetic seal or other bond, such as a heated, unheated or ultrasonic knife and welding or heat sealing apparatus.

The controller module 18 may be used to control the cutting and sealing devices 28 and 30. Various temperature sensors T1, T2, T3 and T4 may provide temperature inputs to the controller module 18. In the illustrated example, temperature sensor T1 is at the sleeve entrance location 30, temperature sensor T2 is at the center of the sterilization chamber 20, temperature sensor T3 is near the access opening 34 of the sterilization chamber 20 and temperature sensor T4 is at the access opening 34. Any suitable locations may be used for the temperature sensors. The controller module 18 may include logic for processing the various temperature inputs and performing an action and/or supplying temperature related input to the power conditioning and control module 14.

A medical instrument 50 is located within the sterilization chamber 20. The medical instrument 50 may or may not be formed of a ferromagnetic material. In some embodiments, for example, the medical instrument 50 may be formed of stainless steel. As illustrated, the sleeving material 24 may be drawn about the medical instrument 50. The sleeving material 24 may include a bottom portion 24a and an upper portion 24b. The bottom portion 24a may be located beneath the medical instrument 50 and the upper portion 24b may be located above the medical instrument 50 thereby at least partially surrounding the medical instrument 50 with the sleeving material 24. The sleeving material 24 is formed of any suitable ferromagnetic foil material. For example, the sleeving material may be formed of iron foil, steel foil and the like.

An openable door 52 may be located at the access opening 34. The door may be hingedly connected to the housing structure 26 at hinge 54 and may be openable manually or automatically (e.g., using an actuator). In some embodiments, the door 52 may include a locking structure 56 that is used to lock the door 52 in its closed position. The locking structure 56 may include a releasable locking device 58 including a actuatable pin 60 and an engageable slot 62 carried by the door 52. The controller module 18 may control the releasable locking device 58 based, for example, on whether the sterilizing system 10 is in a sterilizing operation, temperature of the sterilization chamber 20, etc.

In some embodiment, a sterilization plate 63 may be located in the sterilization chamber 20 that is formed of a ferromagnetic material. The sterilization plate 63 may provide a support surface for the medical instrument 50. In other embodiments, the sterilization plate 63 may not be formed of a ferromagnetic material. In some embodiments, the sterilization plate 63 may be a floor running between sidewalls of the sterilization chamber 20.

The sterilizing system 10 may include a user interface 65 for user control of the sterilizing system 10, which may include buttons, switches, knobs, a touch screen and/or display, a touch pad or keyboard, which may provide a QWERTY layout in one embodiment, a AZERTY or QWERTZ layout in other embodiments. The user interface 65 may include any display devices, speakers, lights, etc. for providing information to a user regarding a sterilizing operation or other information.

In operation, an operator may open the door 52 and unroll an amount of sleeve material 24 from the roll 22 by pulling the sleeve material through the entrance location 30. The sleeve material 24 may be in a tube form and the operator may place the medical instrument 50 inside the sleeve material 24 as shown such that the bottom portion 24a is below the medical instrument 50 and the upper portion 24b is above the medical instrument 50. The operator may then close the door 52 thereby sealing the medical instrument 50 within the sterilization chamber 20.

The operator may then activate the sterilizing system 10 using the user interface 65. The power conditioning and control module 14 may provide AC power to the induction coil 16. The alternating magnetic field (represented by line 64) induces eddy currents within the ferromagnetic sleeve material 24 which leads to Joule heating of the sleeve material 24. Heat from the sleeve material 24 is transferred to the medical instrument 50. In some embodiments, temperatures of greater than about 400° F., such as greater than about 450° F. may be achieved in the sleeve material 24 and the medical instrument 50. In instances where the medical instrument 50 is itself formed of a ferromagnetic material, eddy currents may be induced in the medical instrument 50. Once the predetermined sterilization temperature is reached, in some embodiments, for a predetermined period of time (e.g., as determined using the temperature sensors and the controller module 18), the power conditioning and control module 14 may stop AC power supply to the induction coil 16.

In some embodiments, a vacuum may be introduced within the sleeve material 24 to evacuate the sleeve material after the heating operation. The cutting and sealing devices 28 and 30 may then sever and seal the sleeve material 24 at opposite sides of the medical instrument 50 thereby hermetically sealing the medical instrument 50 within a pouch formed by the sleeve material 24. The operator may then open the door 52 and the medical instrument 50 sealed within the pouch may be removed from the sterilization chamber 20.

Figure 2:
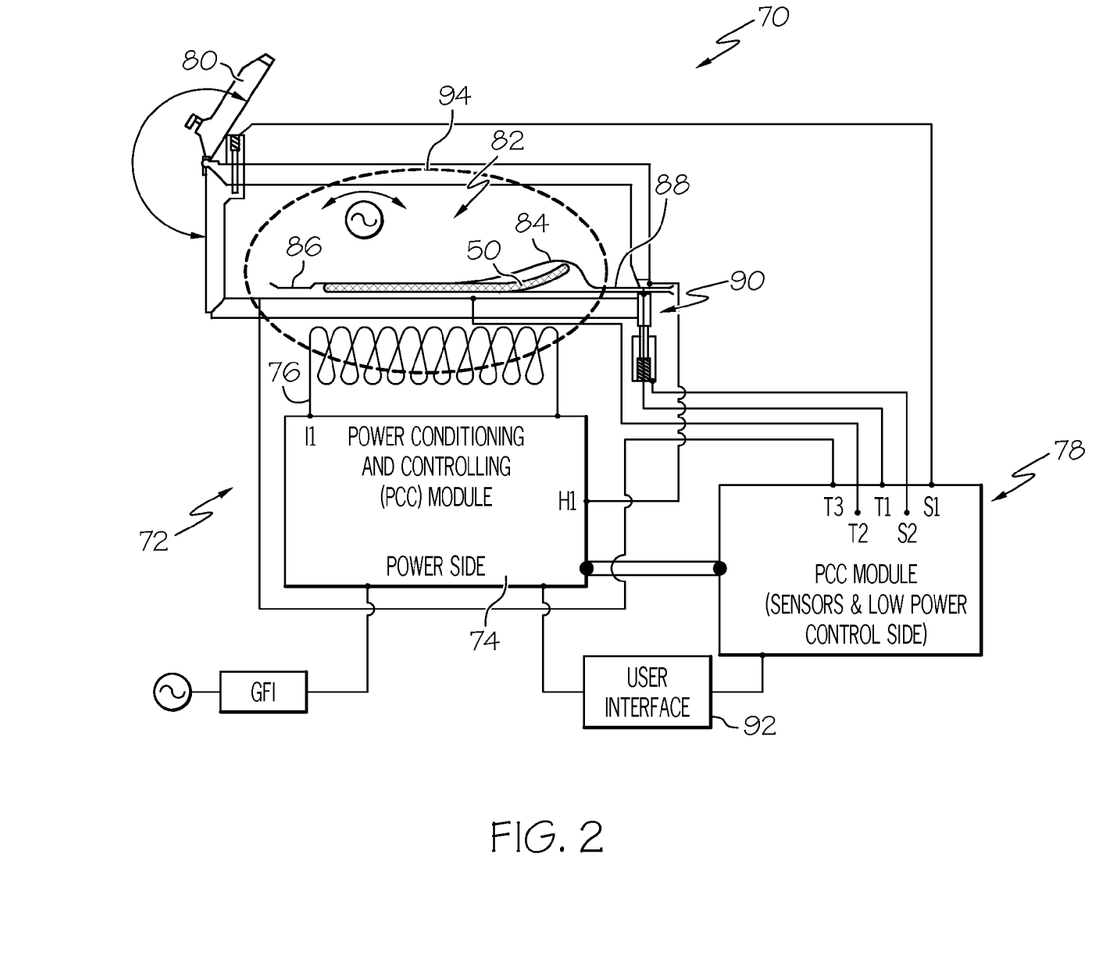
FIG. 2 illustrates a system schematic of a bagging-type sterilizer embodiment using an open-ended bag bagging in conjunction with a single inductively heated surface.

Referring to FIG. 2, an alternative embodiment of a sterilizing system 70 includes many of the same or similar components described above with regard to sterilizing system 10 such as an EMF energy field generator 72 including a power conditioning and control module 74 and an induction coil 76, a controller module 78 that receives inputs from one or more sensors and/or control devices, a door 80 and a sterilization chamber 82. In this embodiment, the medical instrument 50 is located in an open-ended pouch or bag 84 formed of a ferromagnetic foil material. In these embodiments, the bag 84 may be pre-sealed at one end 86 and open at an opposite end 88. The opposite end 88 may be held by a cutting and sealing device 90.

In operation, an operator may open the door 80 and feed the open end 88 of the bag 84 into the cutting and sealing device 90. The operator may then close the door 80 thereby sealing the medical instrument 50 within the sterilization chamber 82.

The operator may then activate the sterilizing system 70 using a user interface 92. The power conditioning and control module 74 may provide AC power to the induction coil 76. The alternating magnetic field (represented by line 94) induces eddy currents within the ferromagnetic bag material which leads to Joule heating of the bag material. Heat from the bag material is transferred to the medical instrument 50. In instances where the medical instrument 50 is itself formed of a ferromagnetic material, eddy currents may be induced in the medical instrument 50. Once the predetermined sterilization temperature is reached, in some embodiments, for a predetermined period of time (e.g., as determined using the temperature sensors and the controller module 78), the power conditioning and control module 74 may stop AC power supply to the induction coil 76.

In some embodiments, a vacuum may be introduced within the bag 84 to evacuate the bag 84 after the heating operation. The cutting and sealing device 90 may then sever and seal the bag 84 at the open end 88 thereby hermetically sealing the medical instrument 50 within the bag 84. The operator may then open the door 80 and the medical instrument 50 sealed within the bag 84 may be removed from the sterilization chamber 82.

Figure 3:
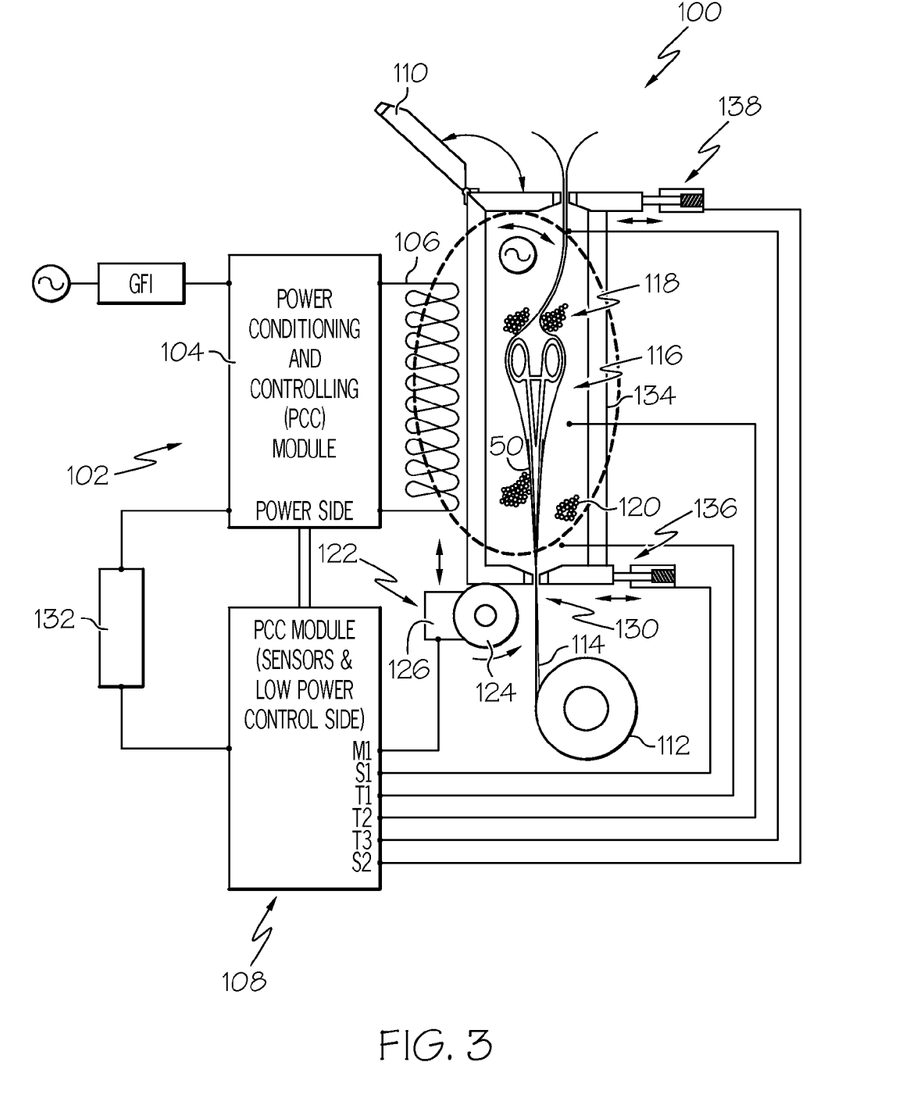
FIG. 3 illustrates a system schematic of a bagging-type sterilizer embodiment using a roll of sleeving material or flattened tube for bagging in conjunction with a single inductive source and a matrix of mechanically-agitated ferromagnetic media.

Referring to FIG. 3, an alternative embodiment of a sterilizing system 100 includes many of the same or similar components described above with regard to sterilizing system 10 such as an EMF energy field generator 102 including a power conditioning and control module 104 and an induction coil 106, a controller module 108 that receives inputs from one or more sensors and/or control devices, a door 110, a roll 112 of continuous sleeve material 114 and a sterilization chamber 116. In this embodiment, a matrix or field 118 of loose ferromagnetic media 120 is provided within the sterilization chamber 116. The ferromagnetic media 120 may be, for example, a plurality of non-spherical ferromagnetic beads (e.g., prisms, cylinders, pyramids, irregular 3-D shapes, and the like).

An agitating system 122 may be provided to mechanically agitate the field 118 of ferromagnetic media 120. The agitating system 122 may include an agitator 124 (e.g., a cam) and a motor 126 or other actuator for rotating the agitator 124. The sterilization chamber 116, in this embodiment, may be capable of controlled movement in response to movement of the agitator 124 against the sterilization chamber 116. For example, the sterilization chamber 116 may include a suspension system that allows for controlled movement of the sterilization chamber 116 in response to forces (e.g., lateral and/or vertical forces) supplied by the agitating system 122.

In operation, an operator may open the door 110 and unroll an amount of sleeve material 114 from the roll 112 by pulling the sleeve material through an entrance location 130. The sleeve material 114 may be in a tube form and the operator may place the medical instrument 50 inside the sleeve material 114 in a fashion similar to that described in FIG. 1. The operator may then close the door 110 thereby sealing the medical instrument 50 within the sterilization chamber 116.

The operator may then activate the sterilizing system 100 using a user interface 132. The agitating system 122 may then be activated by the controller module 108 such that the agitator 124, which is driven by the motor 126 agitates the field 118 of loose ferromagnetic media 120, which distributes the loose ferromagnetic media 120 about the sleeve material 114 and the medical instrument. The power conditioning and control module 104 may provide AC power to the induction coil 106. The alternating magnetic field (represented by line 134) induces eddy currents within the ferromagnetic sleeve material 114 and the ferromagnetic media 120 which leads to Joule heating of the sleeve material 114 and the ferromagnetic media 120. Heat from the ferromagnetic media 120 and the sleeve material 114 is transferred to the medical instrument 50. In instances where the medical instrument 50 is itself formed of a ferromagnetic material, eddy currents may be induced in the medical instrument 50. Once the predetermined sterilization temperature is reached, in some embodiments, for a predetermined period of time (e.g., as determined using the temperature sensors and the controller module 108), the power conditioning and control module 104 may stop AC power supply to the induction coil 106 and the agitating system 122 may be deactivated. In some embodiments, the agitating system 122 may be active throughout the heating operation. In other embodiments, the agitating system 122 may be active for only a portion of the heating operation and/or the agitating system 122 may be active before the heating operation.

In some embodiments, a vacuum may be introduced within the sleeve material 114 to evacuate the sleeve material after the heating operation. Cutting and sealing devices 136 and 138 may then sever and seal the sleeve material 114 at opposite sides of the medical instrument 50 thereby hermetically sealing the medical instrument 50 within a pouch formed by the sleeve material 114. The operator may then open the door 110 and the medical instrument 50 sealed within the pouch may be removed from the sterilization chamber 116.

Figure 4:
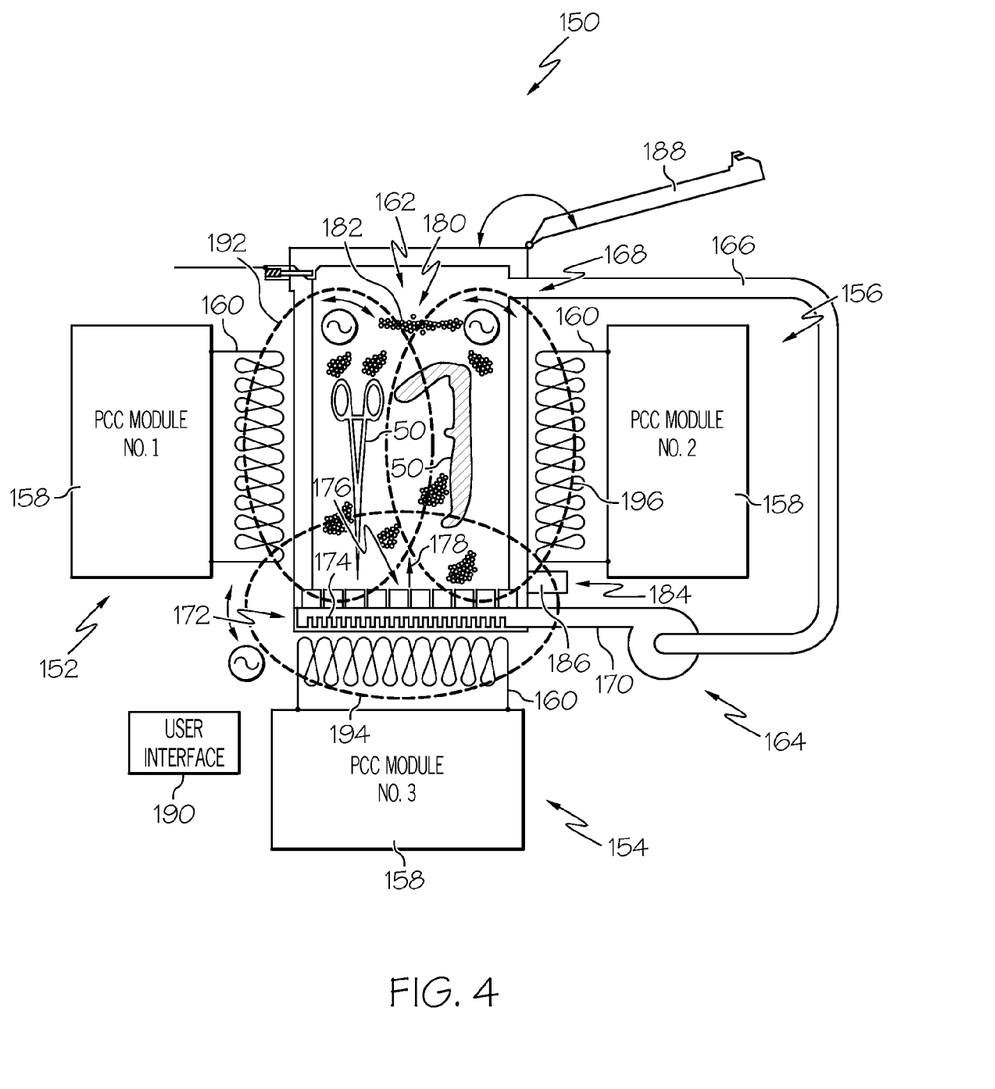
FIG. 4 illustrates a system schematic of an immersion-type sterilizer embodiment using multiple phase-shifted or modulated inductive sources and inductively heated companion surfaces in conjunction with a matrix of pneumatically-agitated, ferromagnetic heat transfer media.

Referring to FIG. 4, another embodiment of a sterilizing system 150 uses multiple phase-shifted or modulated inductive sources and inductively heated companion surfaces in conjunction with a matrix of pneumatically-agitated, ferromagnetic heat transfer media. In this embodiment, multiple EMF field energy generators 152, 154 and 156 form the multiple phase-shifted or modulated inductive sources, each including a power conditioning and control module 158 and an induction coil 160. As above, the sterilizing system 150 may further include a control module that receives inputs from one or more sensors and/or control devices, which is eliminated here for clarity.

The sterilizing system 150 includes a sterilization chamber 162. A gas (e.g., air) superheating system 164 is connected to the sterilization chamber 150. The gas superheating system 164 includes an outlet plenum 166 that is connected to the sterilization chamber 162 at an outlet 168 through which gas exits the sterilization chamber 162 and an inlet plenum 170 that is connected to the outlet plenum 166. The inlet plenum 170 may include a superheating structure 172 such as a fin structure having multiple heating fins 174 that heat the gas flowing by the multiple heating fins 174. The multiple heating fins 174 may be any suitable size and shape for superheating the gas flowing thereby. A fan 176 may be provided for circulating the gas through the superheating system 164 and back into the sterilization chamber 162 represented by arrow 178. The inlet plenum 170 and/or the superheating structure 172 may be formed of a ferromagnetic material that is heated using one or more of the EMF field energy generators 152, 154 and 156.

A matrix or field 180 of loose ferromagnetic media 182 is provided within the sterilization chamber 162. In other embodiments, the media may be non-ferromagnetic. As above with FIG. 3, the ferromagnetic media 182 may be, for example, a plurality of non-spherical ferromagnetic beads (e.g., prisms, cylinders, pyramids, irregular 3-D shapes, and the like).

An agitating system 184 may be provided to mechanically agitate the field 180 of ferromagnetic media 182. The agitating system 184 may include an agitator 186 (e.g., a pneumatic cylinder). As above, the sterilization chamber 162 may be capable of controlled movement in response to movement of the agitator 186 against the sterilization chamber 162. For example, the sterilization chamber 162 may include suspension system that allows for controlled movement of the sterilization chamber 162 in response to forces (e.g., lateral and/or vertical forces) supplied by the agitating system 184.

In operation, an operator may open door 188 and place the medical instruments 50 inside the sterilization chamber 162 (e.g., without use of any ferromagnetic sleeve material). The operator may then close the door 188 thereby sealing the medical instruments 50 within the sterilization chamber 162.

The operator may then activate the sterilizing system 150 using a user interface 190. The agitating system 184 may then be activated by the controller module such that the agitator 186, agitates the field 180 of loose ferromagnetic media 182, which distributes the loose ferromagnetic media 182 about the medical instruments 50. The power conditioning and control modules 158 may provide AC power to their induction coils 160 in a phase-shifted or modulated fashion. The alternating magnetic fields (represented by lines 192, 194 and 196) induces eddy currents within the ferromagnetic media 120 and the superheating structure 172 which leads to Joule heating of the ferromagnetic media 120 and superheating structure 172. Heat from the ferromagnetic media 120 and the sleeve material 114 is transferred to the medical instruments 50 and the surrounding gas. In instances where the medical instrument 50 is itself formed of a ferromagnetic material, eddy currents may be induced in the medical instrument 50. The heated gas is then circulated through the superheating system 164 where the heated gas is further heated to a higher temperature by the superheating structure 172. Once the predetermined sterilization temperature is reached, in some embodiments, for a predetermined period of time (e.g., as determined using temperature sensors and controller module), the power conditioning and control modules 158 may stop AC power supply to their induction coils 160 and the agitating system 184 may be deactivated.

In some embodiments, a vacuum may be introduced within the sterilization chamber 150 to evacuate the sterilization chamber 150 after the heating operation. The operator may then open the door 188 and the medical instruments 50 may be removed from the sterilization chamber 150.

The need to sterilize instruments, containers, and devices is a ubiquitous need in medical, laboratory, and biomedical/industrial applications. Current devices used for such purposes use pressurized, superheated steam; ovens with resistance heating elements, gas ovens, and gamma ray radiation. These methods may be disadvantageous when compared to magnetic induction for several reasons. First, the efficiency of heat transfer is superior with magnetic induction. Magnetic induction is 90% efficiency when compared to the 55% and 50% efficiency for electric resistance coils and gas, respectively. Second, due to the rapid heating, magnetic inductively heated surfaces can reach temperatures in excess of 400° F. more rapidly than an electric resistance coil or gas heat methods. With the ever-increasing cost of fuels, the increased efficiency of magnetic induction incorporated into a sterilizer provides a more efficient method to sterilize instruments and other devices at a total lower cost.

The above-described sterilization systems may have one or more of the following advantages:
1. More efficient heating method of sterilization when using electricity
2. More rapid heating.
3. Suitable for instruments comprised of ferromagnetic and/or non-ferromagnetic materials.
4. Uses available AC power.
5. Suitable for sterilizing either "bagged" or non-bagged instruments & devices.
6. Does not require water (typically distilled or demineralized) or heavy pressure vessels.
7. Safer than traditional autoclave technology which requires the use of superheated and pressurized steam and therefore avoids the risk of explosion of a malfunctioning pressure vessel.
8. Does not require the use of highly dangerous, radioactive gamma ray sources.
9. Lighter weight construction and less operational maintenance required than traditional autoclaves make this device more portable and more useful in developing countries.
10. Higher heat levels than traditional autoclave sterilization can destroy infectious particles such as prions that can survive the autoclave process.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

What is claimed is:

1. A dry heat sterilizing system for use in sterilizing a medical instrument, the sterilizing system comprising:
   a sterilization chamber;
   a foil material configured to be positioned along a medical instrument in the sterilization chamber;
   a field of loose ferromagnetic beads within the sterilization chamber; and
   at least one inductive EMF energy field generator that inductively heats the field of loose ferromagnetic beads during a sterilization operation;
   wherein the field of loose ferromagnetic beads is in thermal communication with the medical instrument during a sterilization operation to transfer heat from the field of loose ferromagnetic beads to the medical instrument.

2. The sterilizing system of claim 1, wherein the at least one inductive EMF energy field generator comprises a power conditioning and control module and an induction coil, the power conditioning and control module providing AC power to the induction coil.

3. The sterilizing system of claim 1 further comprising a medical instrument located within the sterilization chamber and the foil material positioned along the medical instrument.

4. The sterilizing system of claim 3, wherein the foil material is in the form of a sleeve or pouch.

5. The sterilizing system of claim 4 further comprising a sealing device that seals an open end of the sleeve or pouch.

6. The sterilizing system of claim 1, wherein at least some of the ferromagnetic beads are non-spherical.

7. The sterilizing system of claim 1 further comprising an agitating system comprising an agitator that moves the sterilization chamber for agitating the field of loose ferromagnetic beads.

8. The sterilizing system of claim 1 further comprising a control module and a temperature sensor operatively connected thereto, the temperature sensor being located in the sterilization chamber for providing temperature information to the control module.

9. The sterilizing system of claim 8 further comprising: a door that inhibits operator access to the sterilization chamber; and a door lock mechanism that is controlled by the control module.

10. A dry heat sterilizing system for use in sterilizing non-ferromagnetic medical instruments, the sterilizing system comprising:
    a sterilization chamber;
    a field of loose ferromagnetic beads located within the sterilization chamber;
    at least one inductive EMF energy field generator that inductively heats the loose ferromagnetic beads during a sterilization operation; and
    a superheating system having an inlet for receiving heated gas from the sterilization chamber and an outlet for re-introducing heated gas to the sterilization chamber, the superheating system including a superheating structure comprising a ferromagnetic material such that, once inductively heated, the superheating structure transfers heat to the heated gas prior to re-introduction to the sterilization chamber.

11. A dry heat sterilizing system for use in sterilizing a medical instrument, the sterilizing system comprising:
    a sterilization chamber;
    a foil material within the sterilization chamber configured to be positioned along a medical instrument;
    a field of loose ferromagnetic beads within the sterilization chamber; and
    at least one inductive EMF energy field generator comprising a power conditioning and control module and an induction coil, the power conditioning and control module providing AC power to the induction coil;
    wherein the at least one inductive EMF energy field generator is arranged and configured to pass an EMF energy field through the medical instrument to inductively heat the medical instrument during a sterilization operation.

12. The sterilizing system of claim 11, wherein a medical instrument is located within the sterilization chamber and the foil material is positioned along the medical instrument.

13. The sterilizing system of claim 11, wherein the foil material is ferromagnetic.

14. The sterilizing system of claim 11, wherein the foil material is in the form of a sleeve or pouch.

15. The sterilizing system of claim 11 further comprising an agitating system comprising an agitator that moves the sterilization chamber for agitating the field of loose ferromagnetic beads.

16. The sterilizing system of claim 11 further comprising a control module and a temperature sensor operatively connected thereto, the temperature sensor being located in the sterilization chamber for providing temperature information to the control module.

17. The sterilizing system of claim 16 further comprising: a door that inhibits operator access to the sterilization chamber; and a door lock mechanism that is controlled by the control module.

* * * * *